US00PP33427P3

(12) United States Plant Patent
Bunnik

(10) Patent No.: US PP33,427 P3
(45) Date of Patent: Aug. 31, 2021

(54) ***VRIESEA* PLANT NAMED 'BUNVRIOR'**

(50) Latin Name: ***Vriesea* Lindl.**
Varietal Denomination: BUNVRIOR

(71) Applicant: 3B Fundus B.V., Kudelstaart (NL)

(72) Inventor: Bjorn Bunnik, Kudelstaart (NL)

(73) Assignee: 3B Fundus B.V., Kudelstaart (NL)

( * ) Notice: Subject to any disclaimer, the term of this patent is extended or adjusted under 35 U.S.C. 154(b) by 0 days.

(21) Appl. No.: 17/106,577

(22) Filed: Nov. 30, 2020

(65) Prior Publication Data

US 2021/0168983 P1 Jun. 3, 2021

(30) Foreign Application Priority Data

Nov. 30, 2019 (QZ) ..... 2019/3275

(51) Int. Cl.
*A01H 5/02* (2018.01)
*A01H 6/22* (2018.01)

(52) U.S. Cl.
USPC ..... Plt./370
CPC ..... *A01H 6/228* (2018.05)

(58) Field of Classification Search
USPC ..... Plt./370
CPC ..... A01H 6/228
See application file for complete search history.

*Primary Examiner* — Anne Marie Grunberg
(74) *Attorney, Agent, or Firm* — Samuel R. McCoy, Jr.

(57) ABSTRACT

A new and distinct *Vriesea* plant named 'BUNVRIOR' which is characterized by a relatively compact rosette of glossy, dark green foliage that gives rise to a terminal, compound spike inflorescence with distichous flowers held within and above the foliage with an orange bract at the base of each branch of the inflorescence and vibrant orange-red conduplicate bracts with yellow tips, subtending each yellow flower, as well as the stability of these characteristics from generation to generation.

1 Drawing Sheet

Latin name of the genus and species: The Latin name of the genus and species of the novel variety disclosed herein is *Vriesea* Lindl.

Variety denomination: The inventive variety of *Vriesea* disclosed herein has been given the variety denomination 'BUNVRIOR'.

CROSS REFERENCE TO RELATED APPLICATIONS

This application claims priority to the Community Plant Variety Rights application number 2019/3275, filed Nov. 30, 2019, which is herein incorporated by reference.

BACKGROUND OF THE INVENTION

Parentage: The *Vriesea* variety 'BUNVRIOR' is a seedling selection which resulted from a controlled pollination breeding program. In November of 2013, the inventor performed the controlled cross-pollination of a proprietary unnamed *Vriesea* plant, the seed parent, and a second unnamed proprietary *Vriesea* plant, the pollen parent, at a commercial greenhouse in Kudelstaart, the Netherlands. Both parents were developed by the inventor and never released to the public. In April of 2016, the inventor observed one seedling from the cross which exhibited unique foliage and inflorescence characteristics and isolated the plant for further evaluation. Upon confirmation of distinctness and stability, the new *Vriesea* plant was selected for commercialization and given the name 'BUNVRIOR'.

Asexual Reproduction: 'BUNVRIOR' was first asexually propagated by way of vegetative cuttings in July of 2016 and subsequently by way of meristematic tissue culture micropropagation at a commercial tissue culture laboratory in Aalsmeer, the Netherlands. Through 7 subsequent generations, the unique features of this cultivar are stable and reproduced true to type.

SUMMARY OF THE INVENTION

The cultivar 'BUNVRIOR' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'BUNVRIOR'. These characteristics in combination distinguish 'BUNVRIOR' as a new and distinct *Vriesea* cultivar:

1. *Vriesea* 'BUNVRIOR' exhibits a relatively compact rosette of glossy, dark green foliage; and
2. *Vriesea* 'BUNVRIOR' exhibits a terminal, compound spike inflorescence with distichous flowers held within and above the foliage; and
3. *Vriesea* 'BUNVRIOR' exhibits a large, orange bract at the base of each branch of the inflorescence; and
4. *Vriesea* 'BUNVRIOR' exhibits vibrant orange-red conduplicate bracts with yellow tips, subtending each yellow flower.

BRIEF DESCRIPTION OF THE FIGURES

FIG. 1 illustrates, as nearly true as it is reasonably possible to make the same in color photographs of this type, an exemplary plant of 'BUNVRIOR' grown in a commercial greenhouse in Kudelstaart, the Netherlands. This plant is approximately 37 weeks old from the time of mericloning, shown planted in a 12 cm nursery container.

BOTANICAL DESCRIPTION OF THE PLANT

The following observations and measurements made in November of 2020 describe averages from a sample set of six specimens of 37 week-old 'BUNVRIOR' plants grown in 12 cm nursery pots at a commercial greenhouse in Kudelstaart, the Netherlands. Plants were grown under shade cloth and maintained with a 0.8 EC fertigation program with regular overhead irrigation. No chemical pest measures were taken.

Those skilled in the art will appreciate that certain characteristics will vary with older or, conversely, with younger plants. 'BUNVRIOR' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'BUNVRIOR' and comparisons with the parents and most similar commercial variety of *Vriesea* are provided below.

Plant description:

*Growth habit*.—Perennial; monopodial; broad, upright. Leaves arranged in a basal rosette, with no lateral branching, and the inflorescence growing from the center of the basal rosette and held above the foliage.

*Plant form*.—Flattened globular.

*Average height*.—18.4 cm, from the soil level to the top of the foliar plane, and 34.0 to the top of the floral plane.

*Plant spread*.—Average of 38.0 cm.

*Growth rate*.—Moderately fast.

*Plant vigor*.—Moderately vigorous.

*Propagation type*.—Vegetative cuttings.

*Time to initiate roots*.—Approximately 2 to 4 weeks to initiate roots at 22 degrees Celsius.

*Time to produce a rooted cutting*.—Approximately 3 months at 22 degrees Celsius.

*Pest resistance and susceptibility*.—Neither resistance nor susceptibility to typical *Guzmania* pests and diseases has been observed.

*Temperature tolerances*.—USDA Zones 10 to 13; at least tolerant of temperatures to 40 degrees Celsius. High tolerance to rain inundation; high tolerance to wind.

Root system:

*General*.—Thick; medium density.

*Texture*.—Slightly fleshy.

Foliage:

*Arrangement*.—Basal rosette. No stems or lateral branches.

*Attachment*.—Sessile.

*Division*.—Simple.

*Quantity of leaves*.—24.

*Lamina*.—Dimensions — 26.7 cm long and 4.3 cm wide. Thickness — Approximately 0.9 cm. Shape of blade — Ensiform. Aspect — Moderately concave. Attitude — Upright and moderately reflexed. Apex — Apiculate. Base — Sheathing. Margin — Entire; not undulated. Pubescence, texture and luster of adaxial surface — Glabrous, smooth and glossy. Pubescence, texture and luster of abaxial surface — Glabrous, smooth and glossy. Color — Juvenile foliage, adaxial surface — Green, nearest to in between RHS 137A and NN137A. Juvenile foliage, abaxial surface — Nearest to in between green and yellow-green, RHS 137B and 146A. Mature foliage, adaxial surface — Nearest to in between green and yellow-green, RHS NN137A and 146A yet slightly darker. Mature foliage, abaxial surface — Yellow-green, nearest to in between RHS 146A and 147B. Venation — Pattern — Parallel. Mature foliage venation, adaxial surface — Nearest to in between green to yellow-green, RHS NN137A and 146A yet slightly darker. Mature foliage venation, abaxial surface — Yellow-green, nearest to RHS 147A.

*Sheath*.—Sheath length — 7.3 cm. Sheath width — 7.6 cm. Sheath color, adaxial surface — Purple, nearest to in between RHS N77B and N77C, and fading to yellow-green towards the lamina, nearest to 146D. Sheath color, abaxial surface — Purple, nearest to RHS N77B, and fading to yellow-green towards the lamina, nearest to 146D.

Inflorescence:

*Inflorescence arrangement*.—Terminal compound distichous spike.

*Natural flowering season*.—Continuous flowering.

*Time to flower*.—Approximately 6 months.

*Inflorescence quantity*.—One.

*Flowers per inflorescence*.—Average of 90, with 30 open flower and 60 in bud stage and not opening.

*Inflorescence height*.—Approximately 22.5 cm (measured from base of lowest flower to top of upper flower).

*Inflorescence width*.—Average of 10.2 cm, excluding bracts, and 15.4 cm with bracts.

*Peduncle*.—Dimensions — Approximately 23.1 cm long and 0.8 cm in diameter. Attitude — Near vertical. Strength — Strong. Texture and luster — Glabrous, smooth, and moderately glossy. Color — Greyed-green, nearest to RHS 196D, and strongly suffused with greyed-purple, nearest to a mixture of RHS 186B and 186C.

Bud:

*Length*.—Average of 1.7 cm.

*Diameter*.—Average of 0.4 cm.

*Shape*.—Lanceolate.

*Texture and luster*.—Glabrous, smooth, and slightly glossy.

*Color*.—Yellow-green, nearest to RHS 148D; apex is darker, nearest to RHS 154B; base is greyed-yellow, nearest to RHS 160C.

Flower:

*Flower type and form*.—Single; oblanceolate to narrow oblong.

*Attachment*.—Sessile.

*Attitude*.—Upright.

*Height*.—Approximately 0.5 cm.

*Diameter*.—Average of 0.5 cm.

*Depth*.—Approximately 3.0 cm.

*Fragrance*.—No fragrance.

*Lastingness*.—4 weeks.

*Persistent*.—Persistent.

*Petals*.—Quantity of Petals — 3. Arrangement — Rotate; single whorl; petals free. Length — Approximately 2.5 cm. Width — Approximately 0.5 cm. Shape — Oblong Aspect — Concave. Apex — Obtuse. Base — Cuneate. Margin — Entire; not undulated. Pubescence, texture and luster of upper surface — Glabrous, smooth and slightly glossy. Pubescence, texture and luster of lower surface — Glabrous, smooth and slightly glossy. Color when opening, upper surface — Yellow, nearest to RHS 4C; apex is green-yellow, nearest to RHS 1A. Color when opening, lower surface — Yellow, nearest to RHS 4C; apex is darker, nearest to RHS 5B; tipped yellow-green, nearest to RHS 144B. Color when fully opened, upper surface — Yellow, nearest to RHS 4C; apex is green-yellow, nearest to RHS 1A. Color when fully opened, lower surface — Yellow, nearest to RHS 4C; apex is darker, nearest to RHS 5B; tipped yellow-green, nearest to RHS 144B. Fading, upper surface — Not fading. Fading, lower surface — Not fading. Venation color, fully opened, upper surface — No venation is visible. Venation color, fully opened, lower surface — No venation is visible.

*Calyx*.—Shape — Rotate. Length — Average of 3.0 cm. Diameter — Average of 0.55 cm.

*Sepals*.—Quantity — 3 unfused sepals in a single whorl. Arrangement — Rotate. Length — 2.9 cm. Width — 0.5 cm. Shape — Lanceolate. Aspect — Strongly concave. Apex — Bluntly acute. Base — Cuneate. Margin — Entire. Pubescence, texture and luster of upper surface — Glabrous, smooth, and moderately glossy. Pubescence, texture and luster of lower surface — Glabrous, smooth, and moderately glossy. Color when opening, upper surface — Yellow, nearest to in between 10C; darker towards the apex, nearest to RHS 10A. Color when opening, lower surface — Yellow, nearest to in between 10A; darker towards the apex, nearest to RHS 11A. Color when fully opened, upper surface — Yellow, nearest to in between 10C; darker towards the apex, nearest to RHS 10A. Color when fully opened, lower surface — Yellow, nearest to in between 10A; darker towards the apex, nearest to RHS 11A.

*Bract*.—General — One large, colorful bract is present at each node or branch of the inflorescence; one large, colorful bract subtends each individual flower. Bracts at the nodes of the inflorescence — Shape — Obovate. Aspect — Concave. Dimensions — Average of 4.9 cm long, including the sheath, and 2.2 cm wide. Apex — Apiculate. Base — Cuneate. Margins — Entire. Texture and luster, upper surface — Smooth and slightly glossy. Texture and luster, lower surface — Smooth and glossy. Color, upper surface — Greyed-green, nearest to RHS 197C, and strongly suffused with red, nearest to a mixture of RHS 54B and 54C; apex is yellow-green, nearest to RHS 148B. Color, lower surface — Red, nearest to RHS 53B; apex is suffused with yellow-green, nearest to RHS 148A. Venation — No venation is visible. Bracts subtending the individual flowers — Shape — Ovate. Aspect — Conduplicate. Dimensions — Average of 4.6 cm long, including the sheath, and 1.3 cm wide. Apex — Acute. Base — Cuneate. Margins — Entire. Texture and luster, upper surface — Smooth and slightly glossy. Texture and luster, lower surface — Smooth and slightly glossy. Color, upper surface — Orange, nearest to RHS 26B, and suffused with red at the base, nearest to a mixture of RHS 53C and 53D. Color, lower surface — Orange-red, nearest to RHS N30B, and fading to yellow towards the margins, nearest to RHS 21B; base and apex are orange-red, nearest to RHS 34A; tipped with a darker shade of orange-red, nearest to RHS N34A. Venation — No venation is visible.

Reproductive organs:

*Stamens*.—Quantity — 6, on average. Anthers — Attachment — Dorsifixed. Shape — Narrow oblong. Dimensions — 0.7 cm long and 0.18 cm wide. Color — Yellow, nearest to in between RHS 12B and 12C. Filaments — Length — 1.5 cm, on average. Color — White, nearest to RHS 157D. Pollen — Amount — Sparse. Color — Yellow, nearest to a mixture of RHS 12C and 12D.

*Pistil*.—Quantity — 1. Length — 1.9 cm. Style — Length — 1.8 cm. Color — Yellow-green, nearest to RHS 150D. Stigma — Shape — Irregularly club-shaped. Dimensions — Average of 0.1 cm long and 0.25 cm wide. Color — Yellow-green, nearest to RHS 151B. Ovary Color — Yellow-green, nearest to RHS 150D.

Fruit and seed: To date, not observed.

Comparisons With the Parent Plants

Plants of the new cultivar 'BUNVRIOR' differ from the unnamed *Vriesea* seed parent (not patented), by the characteristics described in Table 1.

TABLE 1

| Characteristic | 'BUNVRIOR' | Seed parent. |
|---|---|---|
| Foliage length. | Shorter than the seed parent. | Longer than 'BUNVRIOR'. |
| Branching habit of the inflorescence. | More freely-branched than the seed parent, with 6 to 8 lateral branches. | Not as freely-branching as 'BUNVRIOR'; ranging from 4 to 6 lateral branches. |
| General coloration of the floral bracts. | Orange to orange-red, generally appearing as more of a vibrant orange. | Yellow. |

Plants of the new cultivar 'BUNVRIOR' differ from the unnamed *Vriesea* pollen parent (not patented), by the characteristics described in Table 2.

TABLE 2

| Characteristic | 'BUNVRIOR' | Pollen parent. |
|---|---|---|
| Foliage length. | Longer than the pollen parent. | Shorter than 'BUNVRIOR'. |
| Inflorescence height. | Taller than the pollen parent. | Shorter than 'BUNVRIOR'. |
| General coloration of the floral bracts. | Orange to orange-red, generally appearing as more of a vibrant orange. | Red-orange. |

Comparison With the Most Similar *Vriesea* Cultivar Known to the Inventor

'BUNVRIOR' is similar to the commercial variety *Vriesea* 'TA41' (not patented) in many horticultural characteristics. However, 'BUNVRIOR' differs from 'TA41' in the following characteristics described in Table 3.

TABLE 3

| Characteristic | 'BUNVRIOR' | 'TA41' |
|---|---|---|
| Plant height. | Taller than 'TA41'. | Shorter than 'BUNVRIOR'. |
| Foliage size. | Smaller and narrower than the 'TA41'. | Larger and broader than 'BUNVRIOR'. |
| Foliage luster. | Foliage is not as glossy as that of 'TA41'. | Foliage is glossier than that of 'BUNVRIOR'. |
| Inflorescence size. | Smaller than the 'TA41'. | Larger than 'BUNVRIOR'. |
| General coloration of the floral bracts. | Orange to orange-red, generally appearing as more of a vibrant orange. | More towards a peach color. |

That which is claimed is:

1. A new and distinct variety of *Vriesea* plant named 'BUNVRIOR', substantially as described and illustrated herein.

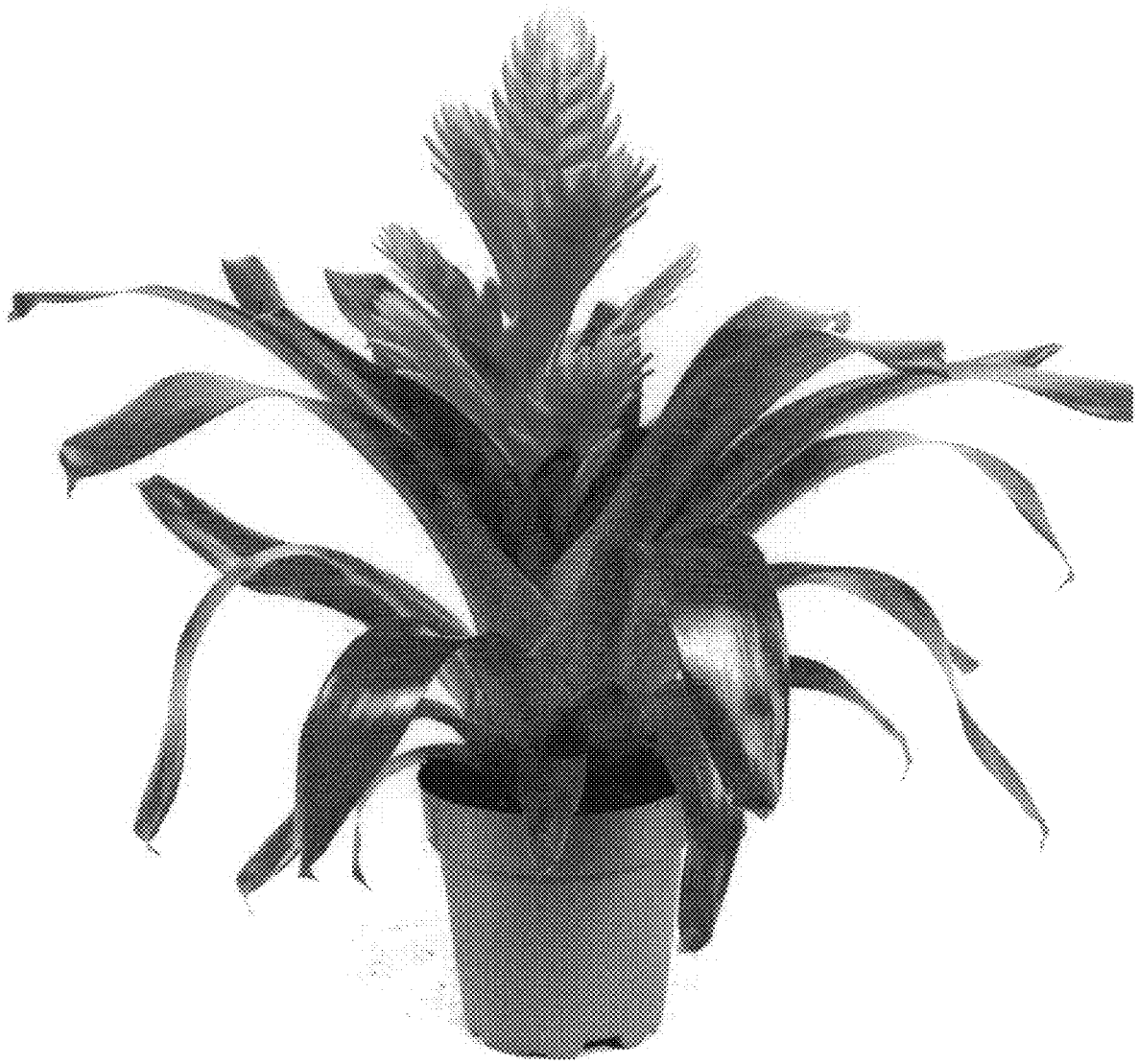

* * * * *